US007129074B2

(12) United States Patent
Sevigny

(10) Patent No.: US 7,129,074 B2
(45) Date of Patent: Oct. 31, 2006

(54) NUCLEOSIDE TRIPHOSPHATE DIPHOSPHOHYDROLASE (NTPDASE 8) AND USES THEREOF

(75) Inventor: Jean Sevigny, Sainte-Foy (CA)

(73) Assignee: Université Laval, Québec (CA)

( * ) Notice: Subject to any disclaimer, the term of this patent is extended or adjusted under 35 U.S.C. 154(b) by 0 days.

(21) Appl. No.: 11/076,982

(22) Filed: Mar. 11, 2005

(65) Prior Publication Data

US 2005/0196798 A1     Sep. 8, 2005

Related U.S. Application Data

(63) Continuation of application No. PCT/CA03/01397, filed on Sep. 15, 2002.

(60) Provisional application No. 60/410,348, filed on Sep. 13, 2002.

(51) Int. Cl.
*C12N 9/14*      (2006.01)
*C12N 1/20*      (2006.01)
*C12N 15/00*     (2006.01)

(52) U.S. Cl. ............... 435/195; 435/252.3; 435/320.1; 536/23.2

(58) Field of Classification Search ............... 435/195, 435/252.3, 320.1; 536/23.2
See application file for complete search history.

(56) References Cited

U.S. PATENT DOCUMENTS 5,798,241 A    8/1998   Beaudoin et al.
6,287,837 B1   9/2001   Beaudoin et al.

FOREIGN PATENT DOCUMENTS

| WO | WO 91/08760 | 6/1991 |
| WO | WO 92/16192 | 10/1992 |
| WO | WO 99/46380 | 9/1999 |
| WO | WO 00/23094 | 4/2000 |
| WO | WO 02/071062 | 9/2002 |

OTHER PUBLICATIONS

Kaczmarek et al., "Identification and characterization of CD39/vascular ATP diphosphohydrolase" J. Biol. Chem. 1996, vol. 271, No. 51, pp. 33116-33122.
J. Sévigny et al. "Identification and Characterization of a Novel Hepatic Canalicular ATP Diphosphohydrolase" 2000 Journal Of Biological Chemistry 275:5640-5647.
Norikatsu Mizumoto et al. CD39 αis the dominant Langerhans cell-associated ectoNTPDase: Modulatory roles in inflammation and immune responsiveness, 2002 Nature Medicine, vol. 8, No. 3, pp. 358-338.
Christian Goepfert et al. "Disordered Cellular Migration and Angiogenesis in cd39-Null Mice" 2001, Circulation, pp. 3109-3115.
Jean Sévigny et al. "Differential catalytic properties and vascular topography of murine nucleoside triphosphate diphosphohydrolase 1 (NTPDase1) and NTPDase2 have implications for thromboregulation.", 2002, Blood, vol. 99, No. 8, pp. 2801-2809.
Herbert Zimmerman "Ectonucleotidases: Some Recent Developments and a Note on Nomenclature", 2001, Drug Development Reasearch, 52:44-56.
Jean Sévigny et al. "Purification of the blood vessel ATP diphosphohydrolase, identification and localization by immunological techniques", 1997, Biochimica et Biophysica Acta 1334 73-88.
Keiichi Enjyoji et al. "Targeted disruption of cd39/ATP diphosphohydrolas results in disordered hemostasis and thromboregulation" 1999, Nature Medicine, vol. 5, No. 9, pp. 1010-1017.
Olaf Guckelberger et al. "Beneficial Effects of CD39/Ecto-Nucleoside Triphosphate Diphosphohudrolase-1 Murine Intestinal Ischemia-Reperfusion Injury".
David J. Pinsky et al. "Elucidation of the thromboregulatory role of CD39/ectoapyrase in the ischemic brain" 2002, The journal of Clinical Investigation, vol. 109, No. 8, pp. 1031-1859.
Aaron J. Marcus "The Endothelial Cell Ecto-ADPase Responsible for Inhibition of Platelet Function is CD39", 1997, The Journal of Clinical Investigation, vol. 99, No. 6, pp. 1351-1360.
Herbert Zimmermann "Extracellular metabolism of ATP and other nucleotides" 2000, Naunyn-Schmiedeberg's Arch Pharmacol, 362:299-309.
Granstein, Richard D. "The skinny on CD39 in immunity and inflammation"2002, Nature medicine, vol. 8, #4, 336-338.
Jennings K. et al., "Purification of Glycoproteins llb and lll from Human Platelet Plasma Membrane and Characterization of a Calcium-dependent Glycoprotein llb-lll complex" 1982, The Journal of Biological Chemistry vol. 257, No. 17, Issue of Sep. 10, pp. 10458-10466.
Albelda S.M. and Buck, C.A., "Integrins and other cell adhesion molecules." 1990, FASEB Journal 4:2868-2880.
Baykov A. A. et al., "A malachite green procedure for orthophosphate determination and its use in alkaline phosphatase-based enzyme immunoassay." 1988, Anal. Biochem. 171:266-270.
Bradford M. M. "A rapid and sensitive method for quantitation of microgram quantities of protein utilizing the principle of protein-dye binding." 1976, Anal. Biochem., 72: 248-254.
Chadwick B. P. and Frischauf A.-M. "The CD39-like Gene Family: Identification of Three New Human Members (CD39L2, CD39L3, CD39L4), Their Murine Homologues, and a Member of the Gene Family from *Drosphila melanogaster*." 1998, Genomics, 50:357-367.
Christoforidis S. et al., "Purification and properties of human placental ATP diphosphohydrolase." 1995, Eur. J. Biochem, 234: 66-74.

(Continued)

*Primary Examiner*—Tekchand Saidha
(74) *Attorney, Agent, or Firm*—Ogilvy Renault, LLP

(57) ABSTRACT

The present invention relates to a new ectohydroxynucleotidase, namely the NTPDasse8, which allows to regulate platelet aggregation or activation involved in the formation of thrombosis and related diseases. The nucleic acid sequence and the corresponding amino acid sequence and uses thereof are described.

2 Claims, 6 Drawing Sheets

OTHER PUBLICATIONS

Collins, F.S. "Generation and initial analysis of more than 15,000 full length human and mouse cDNA sequences." 2002, Proceedings of the National Academy of Sciences of USA, 99(26):16899-16903.

Coté Y.P. et al. "Identification and localization of ATP-diphosphohydrolase (apyrase) in bovine aorta : relevance to vascular tone and platelet aggregation." 1991, Biochimica et Biophysica Acta, 1078:187-191.

Imai, M. et al. "Suppression of ATP diphosphohydrolases/CD39 in human vascular endothelial cells." 1999, Biochemistry, 38:13473-13479.

Jennings L. K. et al. "Purification of glycorproteins llb and lll from human platelet plasma membranes and characterization of a calcium-dependent glycoprotein llb-lll complex." 1982, J. Biol. Chem. 257(17):10458-10466.

Kawai, J. et al. "Functional annotation of a full-length mouse cDNA collection." 2001 Nature, 409:685-690.

Kieffer N. et al. "Platelet membrane glycoproteins: Functions in Cellular interactions." 1990, Annu Rev Cell Biol 6:329-357.

Lebel D. et al. "Characterization and Purification of a Calcium-sensitive ATP Diphosphohydrolase from Pig Pancreas." 1980, The Journal of Biological Chemistry 255(3):1227-1233.

Leclerc M.-C. et al. "Identification, characterization, and immunolocalization of a nucleoside triphosphate diphosphohydrolase in pig liver." 2000, Archives of Biochemistry and Biophysics, 377(2):372-378.

Maliszewski C. R. et al. "The CD39 Lymphoid Cell Activation Antigen—Molecular Cloning and Structural Characterization." 1994, J Immunology 153: 3574-3583.

Newman, S.P. "Therapeutic aerosols." In *Aerosols and the Lung: Clinical and Experimental Aspects*, Butterworths, Chapter 9:197-224.

Plow, E.F. et al. "Expression and function of adhesive proteins on the platelet surface." 1986, In *Biochemistry of Platelets*, Chapter 5:225-256.

Ruoslahti E. "Integrins." 1991, J. Clin. Invest. 87: 1-5.

Yagi K. et al. "Purification of ATP diphosphohydrolase from bovine aorta microsomes." 1989, Eur. J. Biochem, 180:509-513.

SEQUENCE LISTING

```
<160> NUMBER OF SEQ ID NOS: 8

<210> SEQ ID NO 1
<211> LENGTH: 497
<212> TYPE: PRT
<213> ORGANISM: Artificial
<220> FEATURE:
<221> NAME/KEY: PEPTIDE
<222> LOCATION: (1)...(497)
<223> OTHER INFORMATION: Mouse HTPDase8

<400> SEQUENCE: 1

Met Gly Leu Ser Trp Lys Glu Arg Val Phe Met Ala Leu Leu Gly Val
 1               5                  10                  15

Ala Ala Ala Ser Gly Leu Thr Met Leu Val Leu Ile Leu Val Lys Ala
            20                  25                  30

Ile Asn Val Leu Leu Pro Ala Asp Thr Lys Phe Gly Ile Val Phe Asp
        35                  40                  45

Ala Gly Ser Ser His Thr Ser Leu Phe Val Tyr Gln Trp Pro Ala Asn
    50                  55                  60

Lys Glu Lys Asp Thr Gly Val Val Ser Gln Ala Leu Thr Cys Gln Ile
```

-continued

```
                65                  70                  75                  80
Glu Gly Pro Gly Ile Ser Ser Tyr Thr Ser Asp Pro Thr Gln Ala Gly
                    85                  90                  95
Glu Ser Leu Lys Ser Cys Leu Glu Glu Ala Leu Ala Leu Ile Pro Gln
                100                 105                 110
Ala Gln His Pro Glu Thr Pro Thr Phe Leu Gly Ser Thr Ala Gly Met
                115                 120                 125
Arg Leu Leu Ser Gln Lys Asn Ser Ser Gln Ala Arg Asp Ile Leu Ala
                130                 135                 140
Ala Val Ser Gln Thr Leu Ser Lys Ser Pro Val Asp Phe Trp Gly Ala
145                 150                 155                 160
Lys Ile Leu Ala Gly Gln Asp Glu Gly Ala Phe Gly Trp Ile Thr Ile
                165                 170                 175
Asn Tyr Val Leu Gly Met Leu Leu Lys Tyr Ser Ser Gly Gln Trp Ile
                180                 185                 190
Leu Pro Glu Glu Gly Met Leu Val Gly Ala Leu Asp Leu Gly Gly Ala
                195                 200                 205
Ser Thr Gln Ile Ser Phe Val Pro Gln Gly Pro Ile Leu Asp Gln Ser
210                 215                 220
Thr Gln Val Thr Phe Arg Leu Tyr Gly Ala Asn Tyr Ser Val Tyr Thr
225                 230                 235                 240
His Ser Tyr Leu Cys Phe Gly Arg Asp Gln Ile Leu Asn Arg Leu Leu
                245                 250                 255
Ala Lys Leu Ala Gln Asp Arg Leu Ser Ser Gln Val Ala Pro Val Arg
                260                 265                 270
His Pro Cys Tyr His Ser Gly Tyr Gln Ala Ile Leu Pro Leu Ser Ser
                275                 280                 285
Leu Tyr Asp Ser Pro Cys Ile His Thr Thr Asp Ser Leu Asn His Thr
                290                 295                 300
Gln Asn Leu Thr Val Glu Gly Thr Gly Asp Pro Gly Asn Cys Val Val
305                 310                 315                 320
Ala Leu Arg Ser Leu Phe Asn Phe Ser Ser Cys Lys Gly Gln Lys Asp
                325                 330                 335
Cys Ala Phe Asn Gly Ile Tyr Gln Pro Pro Val His Gly Gln Phe Tyr
                340                 345                 350
Ala Phe Ser Asn Phe Tyr Tyr Thr Phe His Phe Leu Asn Leu Thr Ser
                355                 360                 365
Arg Gln Ser Leu Asn Thr Val Asn Asp Thr Val Trp Lys Phe Cys Gln
                370                 375                 380
Lys Pro Trp Lys Leu Val Glu Val Ser Tyr Pro Gly Gln Glu Arg Trp
385                 390                 395                 400
Leu Arg Asp Tyr Cys Ala Ser Gly Leu Tyr Ile Leu Val Leu Leu Leu
                405                 410                 415
Glu Gly Tyr Lys Phe Ser Glu Glu Thr Trp Pro Asn Ile Gln Phe Gln
                420                 425                 430
Lys Gln Ala Gly Asp Thr Asp Ile Gly Trp Thr Leu Gly Phe Met Leu
                435                 440                 445
Asn Leu Thr Gly Met Ile Pro Ala Glu Ala Pro Thr His Trp Arg Ala
450                 455                 460
Gln Ser Tyr Ser Ile Trp Thr Ala Gly Val Val Phe Ala Val Leu Thr
465                 470                 475                 480
Leu Val Ala Ile Leu Gly Ala Ala Ala Ile Gln Ile Phe Trp Thr Gln
                485                 490                 495
```

Asp

<210> SEQ ID NO 2
<211> LENGTH: 1494
<212> TYPE: DNA
<213> ORGANISM: Artificial
<220> FEATURE:
<221> NAME/KEY: allele
<222> LOCATION: (1)...(14)
<223> OTHER INFORMATION: mouse ENTPD8

<400> SEQUENCE: 2

| | | | | | |
|---|---|---|---|---|---|
| atgggactct | cctggaagga | acgggtcttc | atggctctgt | tgggagttgc | agcagcctct | 60 |
| ggcctcacca | tgctcgtcct | catcctggtg | aaggcaatca | atgttctctt | gcctgcagac | 120 |
| accaagtttg | ggattgtgtt | tgatgccggc | tcctcccaca | catccctgtt | tgtgtaccag | 180 |
| tggccagcaa | acaaggagaa | ggacacagga | gtggtcagcc | aggccctgac | ttgccagata | 240 |
| gaaggacctg | gaatctcttc | ctatacctct | gacccgacac | aggctgggga | aagcctgaag | 300 |
| agctgcctgg | aggaggcgct | ggcgttgatc | ccacaggccc | agcatccaga | gacgcccaca | 360 |
| ttcttggggt | ccacagcagg | aatgaggctg | ctcagccaga | gaacagctc | tcaggcaaga | 420 |
| gacatcctag | ctgcagtctc | ccagacacta | agcaagtctc | ctgtggattt | tgggggtgct | 480 |
| aagatcttgg | ctgggcagga | tgaaggtgcc | tttggttgga | tcaccatcaa | ctatgtcctg | 540 |
| ggaatgctcc | tgaagtattc | ctctggacag | tggatcctgc | ctgaagaggg | gatgctagtt | 600 |
| ggtgctctgg | accttggtgg | agcctccacg | cagatcagct | tcgtgcctca | gggccccatc | 660 |
| ctggaccaga | gcacccaagt | caccttccgc | ctgtacggtg | ccaactacag | tgtctacact | 720 |
| cacagctacc | tctgctttgg | gcgggaccag | atcctgaaca | ggctcctggc | taagctggca | 780 |
| caggacaggt | tgagcagcca | ggtggccccg | gtcagacacc | catgctacca | cagtggctac | 840 |
| caggccatac | tgccactgag | ttccttgtat | gactcaccct | gcatccacac | tacagattcc | 900 |
| ctgaaccaca | cccagaacct | cacagttgaa | gggacaggcg | accctgggaa | ctgtgtggta | 960 |
| gctctccgaa | gtctcttcaa | cttctccagc | tgtaagggcc | agaaggattg | tgctttcaat | 1020 |
| ggcatctacc | agcctcctgt | gcacggccag | ttctatgcat | tttccaactt | ttactacacc | 1080 |
| ttccatttcc | tgaacctcac | gtccaggcaa | tcactgaaca | ctgtcaacga | cactgtctgg | 1140 |
| aagttctgtc | agaaaccctg | gaaactggtg | gaagtcagct | atcctgggca | ggagcgctgg | 1200 |
| ttacgggact | actgtgcctc | gggtctgtac | atcctcgtat | tgctgctgga | gggctacaaa | 1260 |
| ttcagtgagg | agacctggcc | caacatccag | ttccagaagc | aggcaggtga | cacagacatt | 1320 |
| ggctggacac | tgggcttcat | gctgaacctg | acaggcatga | ttccagctga | ggcaccgacc | 1380 |
| cactggcggg | ctcagagcta | cagcatctgg | acggctggag | tagtattcgc | agtgctgacc | 1440 |
| cttgtggcca | ttcttggggc | agctgccatc | cagatcttct | ggacccagga | ctag | 1494 |

<210> SEQ ID NO 3
<211> LENGTH: 495
<212> TYPE: PRT
<213> ORGANISM: Artificial
<220> FEATURE:
<221> NAME/KEY: PEPTIDE
<222> LOCATION: (1)...(495)
<223> OTHER INFORMATION: Human NTPDase8

<400> SEQUENCE: 3

Met Gly Leu Ser Arg Lys Glu Gln Val Phe Leu Ala Leu Leu Gly Ala
 1               5                  10                  15

```
Ser Gly Val Ser Gly Leu Thr Ala Leu Ile Leu Leu Val Glu Ala
         20                  25                  30

Thr Ser Val Leu Leu Pro Thr Asp Ile Lys Phe Gly Ile Val Phe Asp
         35                  40                  45

Ala Gly Ser Ser His Thr Ser Leu Phe Leu Tyr Gln Trp Pro Ala Asn
         50                  55                  60

Lys Glu Asn Gly Thr Gly Val Val Ser Gln Ala Leu Ala Cys Gln Val
 65                  70                  75                  80

Glu Gly Pro Gly Ile Ser Ser Tyr Thr Ser Asn Ala Ala Gln Ala Gly
                     85                  90                  95

Glu Ser Leu Gln Gly Cys Leu Glu Glu Ala Leu Val Leu Ile Pro Glu
                100                 105                 110

Ala Gln His Arg Lys Thr Pro Thr Phe Leu Gly Ala Thr Ala Gly Met
                115                 120                 125

Arg Leu Leu Ser Arg Lys Asn Ser Ser Gln Ala Arg Asp Ile Phe Ala
130                 135                 140

Ala Val Thr Gln Val Leu Gly Arg Ser Pro Val Asp Phe Trp Gly Ala
145                 150                 155                 160

Glu Leu Leu Ala Gly Gln Ala Glu Gly Ala Phe Gly Trp Ile Thr Val
                165                 170                 175

Asn Tyr Gly Leu Gly Thr Leu Val Lys Tyr Ser Phe Thr Gly Glu Trp
                180                 185                 190

Ile Gln Pro Pro Glu Glu Met Leu Val Gly Ala Leu Asp Met Gly Gly
            195                 200                 205

Ala Ser Thr Gln Ile Thr Phe Val Pro Gly Gly Pro Ile Leu Asp Lys
        210                 215                 220

Ser Thr Gln Ala Asp Phe Arg Leu Tyr Gly Ser Asp Tyr Ser Val Tyr
225                 230                 235                 240

Thr His Ser Tyr Leu Cys Phe Gly Arg Asp Gln Met Leu Ser Arg Leu
                245                 250                 255

Leu Val Gly Leu Val Gln Ser Arg Pro Ala Ala Leu Leu Arg His Pro
                260                 265                 270

Cys Tyr Leu Ser Gly Tyr Gln Thr Thr Leu Ala Leu Gly Pro Leu Tyr
        275                 280                 285

Glu Ser Pro Cys Val His Ala Thr Pro Pro Leu Ser Leu Pro Gln Asn
        290                 295                 300

Leu Thr Val Glu Gly Thr Gly Asn Pro Gly Ala Cys Val Ser Ala Ile
305                 310                 315                 320

Arg Glu Leu Phe Asn Phe Ser Ser Cys Gln Gly Gln Glu Asp Cys Ala
                325                 330                 335

Phe Asp Gly Val Tyr Gln Pro Pro Leu Arg Gly Gln Phe Tyr Ala Phe
                340                 345                 350

Ser Asn Phe Tyr Tyr Thr Phe His Phe Leu Asn Leu Thr Ser Arg Gln
                355                 360                 365

Pro Leu Ser Thr Val Asn Ala Thr Ile Trp Glu Phe Cys Gln Arg Pro
        370                 375                 380

Trp Lys Leu Val Glu Ala Ser Tyr Pro Gly Gln Asp Arg Trp Leu Arg
385                 390                 395                 400

Asp Tyr Cys Ala Ser Gly Leu Tyr Ile Leu Thr Leu Leu His Glu Gly
                405                 410                 415

Tyr Gly Phe Ser Glu Glu Thr Trp Pro Ser Leu Glu Phe Arg Lys Gln
                420                 425                 430
```

-continued

```
Ala Gly Gly Val Asp Ile Gly Trp Thr Leu Gly Tyr Met Leu Asn Leu
            435                 440                 445

Thr Gly Met Ile Pro Ala Asp Ala Pro Ala Gln Trp Arg Ala Glu Ser
    450                 455                 460

Tyr Gly Val Trp Val Ala Lys Val Val Phe Met Val Leu Ala Leu Val
465                 470                 475                 480

Ala Val Val Gly Ala Ala Leu Val Gln Leu Phe Trp Leu Gln Asp
                485                 490                 495
```

<210> SEQ ID NO 4
<211> LENGTH: 1485
<212> TYPE: DNA
<213> ORGANISM: Artificial
<220> FEATURE:
<221> NAME/KEY: allele
<222> LOCATION: (1)...(1485)
<223> OTHER INFORMATION: Human ENTPD8

<400> SEQUENCE: 4

| | | |
|---|---|---|
| atgggcctgt cccggaagga gcaggtcttc ttggccctgc tgggggcctc gggggtctca | 60 |
| ggcctcacgg cactcattct cctcctggtg gaggccacca gcgtgctcct gcccacagac | 120 |
| atcaagtttg ggatcgtgtt tgatgcgggc tcctcccaca cgtccctctt cctgtatcag | 180 |
| tggccggcga acaaggagaa tgcacgggt gtggtcagcc aggccctggc ctgccaggtg | 240 |
| gaagggcctg gaatctcctc ctacacttct aatgctgcac aggctggtga gagcctgcag | 300 |
| ggctgcttgg aggaggcgct ggtgctgatc cagaggcccc agcatcggaa acacccacg | 360 |
| ttcctggggg ccacggctgg catgaggttg ctcagccgga agaacagctc tcaggccagg | 420 |
| gacatctttg cagcagtcac ccaggtcctg gccggtctc ccgtggactt ttgggggtgcc | 480 |
| gagctcctgg ccgggcaggc cgaaggtgcc tttggttgga tcactgtcaa ctacggcttg | 540 |
| gggacgctgg tcaagtactc cttcactgga aatggatcc agcctccgga ggagatgctg | 600 |
| gtgggtgccc tggacatggg aggggcctcc acccagatca cgttcgtgcc tgggggcccc | 660 |
| atcttggaca gagcaccca ggccgatttt cgcctctacg gctccgacta cagcgtctac | 720 |
| actcacagct acctgtgctt tggacgggac cagatgctga gcaggctcct cgtggggctg | 780 |
| gtgcagagcc gccggctgc cctgctccgt cacccgtgct acctcagcgg ctaccagacc | 840 |
| acactggccc tgggcccgct gtatgagtca ccctgtgtcc acgccacgcc ccgctgagc | 900 |
| ctcccccaga acctcacagt tgaagggaca ggcaaccctg gagcctgcgt ctcagccatc | 960 |
| cgggaacttt tcaacttctc cagctgccag ggccaggagg actgcgcctt tgacggggtc | 1020 |
| taccagcccc cgctgcgggg ccagttctat gccttctcca acttctacta caccttccac | 1080 |
| ttcctgaacc tcacctccag gcagcccctg agcacggtca acgccaccat ctgggagttt | 1140 |
| tgccagaggc cctggaaact ggtggaggcc agctaccctg gcaggaccg ctggctgcgg | 1200 |
| gactactgtg cctcaggcct gtacatcctc accctcctgc acgagggcta cgggttcagc | 1260 |
| gaggagacct ggcccagcct cgagttccga aagcaggcgg gcgtgtggga cattggctgg | 1320 |
| acactgggct acatgctgaa cctgaccggg atgatcccgg ccgatgcgcc ggctcagtgg | 1380 |
| cgggcagaga gctacggcgt ctgggtggcc aaagtggtgt tcatggtgct ggccctggtg | 1440 |
| gcggtggtgg gggctgcctt ggtccagctc ttctggttgc aggac | 1485 |

<210> SEQ IDNO 5
<211> LENGTH: 20
<212> TYPE: DNA
<213> ORGANISM: Artificial

```
<220> FEATURE:
<221> NAME/KEY: primer_bind
<222> LOCATION: (1)...(20)
<223> OTHER INFORMATION: Sense PCR primer 1

<400> SEQUENCE: 5
ggagacgggg tgtggaggac                                              20

<210> SEQ ID NO 6
<211> LENGTH: 20
<212> TYPE: DNA
<213> ORGANISM: Artificial
<220> FEATURE:
<221> NAME/KEY: primer_bind
<222> LOCATION: (1)...(20)
<223> OTHER INFORMATION: Antisense PCR primer 2

<400> SEQUENCE: 6
ggggttcata agggcaggca                                              20

<210> SEQ ID NO 7
<211> LENGTH: 20
<212> TYPE: DNA
<213> ORGANISM: Artificial
<220> FEATURE:
<221> NAME/KEY: primer_bind
<222> LOCATION: (1)...(20)
<223> OTHER INFORMATION: Sens PCR primer 3

<400> SEQUENCE: 7
gtaggtggag acgggtgtg                                               20

<210> SEQ ID NO 8
<211> LENGTH: 20
<212> TYPE: DNA
<213> ORGANISM: Artificial
<220> FEATURE:
<221> NAME/KEY: primer_bind
<222> LOCATION: (1)...(20)
<223> OTHER INFORMATION: Antisense PCR primer 4

<400> SEQUENCE: 8
gggttcataa gggcaggcat                                              20
```

NUCLEOSIDE TRIPHOSPHATE DIPHOSPHOHYDROLASE (NTPDASE 8) AND USES THEREOF

CROSS-REFERENCE TO RELATED APPLICATIONS

This application claims priority under 35USC§119(e) of U.S. provisional patent application Ser. No. 60/410,348 filed on Sep. 13, 2002 and this application is a continuation of PCT patent application serial number PCT/CA2003/001397 filed on Sep. 15, 2002, designating the United States and now pending, the specifications of which are hereby incorporated by reference.

TECHNICAL FIELD

The present invention relates to nucleic acid sequences and related proteins to modulate the adhesion of platelets in blood. More particularly, the invention allows for inhibiting partially or totally the formation of thrombosis and related physiological diseases of causes.

BACKGROUND ART

Nucleosides play significant roles in different body systems, including the nervous and the vascular systems. Their specific functions in these systems is determined by the presence of purine and pyrimidine receptors which react with triphosphate nucleosides and their derivatives at the surface of numerous cell types. The presence in the vascular system of both ectoATPase and ectoADPase activities, that cleave tri- and diphosphate nucleosides respectively, has been known for many years. By their location and kinetic properties, these different catalytic activities could influence these systems. Both activities were previously attributed to two distinct enzymes. These activities were characterized and showed that, in bovine aorta, a single enzyme was responsible for the sequential hydrolysis of ATP and ADP.

The enzyme responsible for that sequential cleavage of the γ and β phosphate residues of polyphosphorylated nucleosides are commonly called nucleoside triphosphate diphosphohydrolases (NTPDase) or apyrases (EC 3.6.1.5). These enzymes are generally activated in the presence of divalent cations $Ca^{+2}$ or $Mg^{+2}$, while sodium azide inhibits their activity azide is an inhibitor of NTPDase1 and a few other NTPDase but not all of them. The catalytic site of these enzymes is generally exposed to extracytoplasmic spaces (ectoenzymes).

In plants, NTPDase enzymes are found in the cytoplasm, in soluble or membrane-associated forms, and are generally more active in acidic conditions. Although their precise function remains unknown, some evidences suggest their implication in the biosynthesis of carbohydrates. At the opposite, the activity of NTPDases is higher at neutral or alkaline pH in invertebrates species, where they principally shown to act as antihemostatic agents in saliva and in salivary glands of hematophagous insects.

In vertebrates, a limited number of studies have already defined a diversity of NTPDases. The first mammalian NTPDase has been isolated from pancreas and was further identified in other tissues, including bovine aorta. It is recognized in the art that NTPDase may be the object of other nomenclature. For exaple, NTPDase1 may refers to vascular ATPDase or CD39.

Nucleosides and thus, NTPDases, contribute to the vascular system homeostasis. Extracellular nucleosides present in the blood due to, e.g., arterial vascular injury can influence cardiac function, vasomotor responses, inflammatory processes, thrombosis, and platelet activation. To maintain blood fluidity and flow, the normal vascular endothelium inhibits coagulation and platelet activation and promotes fibrinolysis. Quiescent endothelial cells are considered to directly express natural anticoagulants and thromboregulatory factors, therefore preventing thrombosis, which usually develops as a consequence of overwhelming these antithrombotic mechanisms. This may occur following the heightened production of locally produced mediators, including cytokines, activated complement components and particularly extracellular nucleotides. In the bovine aorta, NTPDase1 was found to be associated with smooth muscle cells and endothelial cells and could inhibit ADP-induced platelet aggregation. It was further showed that concurrent addition of a semi purified fractin of NTPDase and ATP to platelet-rich plasma resulted in an immediate dose-dependent platelet aggregation caused by the accumulation of ADP, followed by a slow desaggregation attributable to its hydrolysis into AMP. In the absence of NTPDase, ATP does not induce any aggregation while ADP initiates an aggregation which extent is limited by the ADPase activity of the enzyme.

Mechanism of nucleosides actions in blood vessels implicates, between others, the binding to and stimulation of purinergic/pyrimidinergic type-2 (P2) receptors. This stimulation P2Y receptors initiates G protein-coupled signaling pathways and results in activation of platelets, endothelial cells (ECs), monocytes/macrophages, and leukocytes and could culminate in vascular thrombosis and inflammation in vivo. ATP and ADP regulation of platelet aggregation appear to occur through the concomitant activation of platelet $P2Y_1$ and $P2Y_{12}$ receptors. Indeed ADP is a major platelet recruiting and activating factor, whereas ATP acts as a weak competitive antagonist of ADP for platelet P2 receptors. This latter protective action of ATP may limit the formation of intravascular platelet aggregation and help localize thrombus formation to areas of vascular damage. NTPDases also attenuate the aggregation elicited collagen and low level of by thrombin but not by the platelet activating factor (PAF), the first two agonist effects being caused by a release of platelet ADP. It has therefore been suggested that NTPDase had a dual role in regulating platelet activation. By converting ATP released from damaged vessel cells into ADP, the enzyme induced platelet aggregation at the sites of vascular injury. By converting ADP released from aggregated platelets and/or from hemolyzed red blood cells to AMP, the NTPDase could inhibit or reverse platelet activation, and consequently limit the growth of platelet thrombus at the site of injury.

Platelets are particles found in whole blood that initiate and provide the structural basis for the haemostatic plug necessary to stop bleeding. Platelets depend on adhesive interactions with extracellular proteins and other cells for proper function. The external platelet plasma membrane surface is covered with a variety of membrane bound glycoproteins, many of which have adhesive functions. Perhaps the most abundant platelet membrane adhesive proteins belong to the integrin superfamily which include the glycoproteins; GP $I_b$ $III_a$, GP $I_a$ $II_a$, GP $I_c$ $II_a$, GP $I_b$ IX, and the fibronectin and vitronectin receptors. Each integrin receptor is an heterodimer displaying characteristic affinity and specificity toward various extracellular matrix proteins such as; von Willebrand factor (vWF), collagen, entactin, tenascin, fibronectin (Fn), vitronectin (Vn), and laminin, as well as fibrinogen (Fg) and thrombospondin. The most abundant integrin found on normal platelet surfaces is GP II$_b$ et GPIII$_a$ comprising about 50,000 molecules per platelet, representing about 2% of the total platelet protein. GP II$_b$ III$_a$ is a non-covalent, calcium ion dependent heterodimer complex and restricted in distribution to platelets and other cells of the megakaryocytic lineage. On activated platelets, GP II$_b$ III$_a$ binds a number of adhesive proteins with varying affinities; fibrinogen, fibronectin, von Willebrand factor, vitronectin and thrombospondin. It is believed the most important interactions mediating platelet aggregation involve GP II$_b$ III$_a$ binding with the trinodular fibrinogen and, to a lesser extent, with the filamentous von Willebrand factor.

Platelets are key components of all blood clots propagating within the arterial circulation and thus are an obvious therapeutic target in attempts to inhibit coronary artery thrombosis. Despite currently available therapies, a significant number of ischemic events, such as myocardial infarction, stroke, and death, occur each year. These events are generally the result of blood clots blocking the arteries supplying oxygen to heart or brain tissue. Therefore, there exists a need for therapeutics that effectively regulate platelet activation for the purpose of controlling platelet aggregation.

Angiogenesis is also a highly complex multistep phenomenon that incorporates both formation of new capillaries and expansion or extension of existing blood vessels. An associated increased permeability to plasma solutes results in the deposition of a provisional matrix in which fibrin is a major component. New vessel growth may be modulated by monocyte/macrophages that secrete angiogenic factors and metalloproteases that facilitate endothelial cell migration. Supporting cells are also essential for new vessel growth and angiogenesis, for example, smooth muscle cells in vascular maturation and arteriogenesis and pericytes in the protection of newly developing endothelial cell-lined tubes from rupture and regression.

In this context, UTP has been shown to be mitogenic and chemotactic for endothelial cells in vitro. Interestingly, binding of angiostatin, a proteolytic fragment of plasminogen and potent antagonist of angiogenesis, to ATP synthase expressed on endothelial cells, has been shown to mediate antiangiogenic effects.

To decipher the mechanisms of such interactions, the role of nucleotides in angiogenesis cd39-null (or Entpd1)mouse model, in which aberrant regulation of nucleotide P2 receptors has been observed, was investigated. CD39 (also referred to as nucleoside triphosphate diphosphohydrolase-1 (NTPDase1) was shown to be the major vascular endothelial membrane ectonucleotidases and to hydrolyse nucleoside triphosphates and diphosphates, ultimately to the nucleoside analogues; these products having mitogenic effects on endothelial cells in vitro. Because angiogenesis is critical to the progression of various diseases, for example, cancer, rheumatoid arthritis, and diabetic retinopathy, there exists a need for compounds capable of preventing or reducing angiogenesis in patients suffering from an angiogenesis-associated condition. NTPDase1/CD39 could now be used to reduce platelet aggregation, thrombogenicity as well as angiogenesis. However, the solubilization of the protein actually lead to a decrease in nucleoside phosphohydrolase activity. It would thus be highly desirable to be provided with a stable NTPDase for the treatment of prevention of diseases related to blood clotting or angiogenesis.

While some products related to ectohydroxynucleotides as described before exist in the art, there is still place for new molecules allowing platelet aggregation modulation and/or control in different physiological normal or pathological conditions.

DISCLOSURE OF THE INVENTION

One object of the present invention is to provide an isolated nucleoside triphosphate diphosphohydrolase (NTPDase) from a mammalian tissue characterized in that it comprises the amino acid sequence SEQ ID NO:1 or SEQ ID NO:3, a functional fragment thereof, or an amino acid sequence having at least eighty percent (70%) homology with said isolated and purified NTPDase. Preferentially, the homology level at least of 80%.

Another object is to provide an isolated nucleic acid molecule consisting of a nucleotide sequence selected from the group consisting of:
a nucleotide sequence encoding for a peptide comprising the amino acid sequence of SEQ ID NO:1 or SEQ ID NO:3;
a nucleotide sequence consisting of SEQ ID NO:2 or SEQ ID NO:4; and
a nucleotide sequence complementary to at least 70% of a nucleotide sequence of a) or b).

The nucleotide sequences a), b) or c) encode for a peptide having ectonucleotidase activity.

Also, the nucleic acid expression vector may comprise a nucleic acid molecule as defined herein in operative association with a promoter sequence. The promoter can be an inducible or an ubiquitous promoter.

A further object of the invention is to provide a host cell containing the expression vector as defined herein. The host cell is preferably an eukaryotic cell.

Another object of the invention is to provide an isolated peptide comprising the amino acid sequence SEQ ID NO:1, a functional fragment or an analog thereof, said isolated peptide having an ectonucleotidase activity.

Particularly, one object of the present invention is to provide an isolated polynucleotide consisting of a nucleotide sequence set forth in SEQ ID NO:2.

In accordance with the present invention, there is provided a method for modulating at least one biological reaction selected from the group consisting of platelet aggregation, thrombosis, emboli, and angiogenesis, said method comprising depositing in blood or a medium comprising blood an amount sufficient of a peptide encoded by a nucleic acid molecule or an isolated peptide as defined herein under condition allowing the modulation of platelet aggregation, thrombosis, or emboli.

Also, another object of the invention is to provide a method for modulating at least one biological reaction selected from the group consisting of platelet aggregation, thrombosis, emboli, and angiogenesis, comprising administrating to a patient an expression vector as defined herein.

Alternatively, there is provided a method for modulating at least one biological reaction selected from the group consisting of platelet aggregation, thrombosis, emboli, and angiogenesis, comprising administrating to a patient a partial expression vector without promoter and designed to incorporate a transcriptionnally active genomic region of a cell, said partial expression being transcribed under the control of a promoter endogenous to said genomic region.

The sequence complementary to the NTPDase8 molecule of the present invention can be obtained from mammalian tissue from which the NTPDase is isolated, as for example from a human (SEQ ID NO:3), a porcine, a bovine, a primate, a caprine, an ovine, an equine, a murine, a canine, a grouse or a feline tissue.

Another object of the present invention is to provide an isolated nucleotide sequence encoding the amino acid sequence of the isolated NTPDase described above or the complementary nucleotide sequence thereof, wherein said isolated nucleotide sequence is a gene, a complementary DNA (cDNA), a messenger RNA (mRNA), a complementary RNA (cRNA) or a fragment thereof.

A further object of the present invention is to provide a recombinant expression vector comprising a promoter sequence and a nucleotide sequence encoding the amino acid sequence of the isolated NTPDase described above.

Also, one object of the present invention is to provide a recombinant host cell, transformed or transfected with said recombinant expression vector comprising a nucleotide sequence encoding the amino acid sequence of the isolated NTPDase.

In one object of the present invention, there is provided a method for modulating platelet aggregation, thrombogenicity or angiogenesis which comprises an administration of a NTPDase.

A further object of the present invention is to provide a composition for modulating platelet aggregation, thrombogenicity or angiogenesis wherein said composition comprises the isolated NTPDase as active ingredient. The active ingredient can be found alone or in combination with an acceptable carrier.

In a further object of the present invention, there is provided a method for converting ATP into ADP and/or ADP into AMP comprising an administration of the NTPDase described herein.

Another object of the present invention is to provide A composition for converting ATP into ADP and/or ADP into AMP comprising the NTPDase described herein, together with a pharmaceutically acceptable carrier.

"Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

BIEF DESCRIPTION OF DRAWINGS

MODES OF CARRYING OUT THE INVENTION

Figure 1:
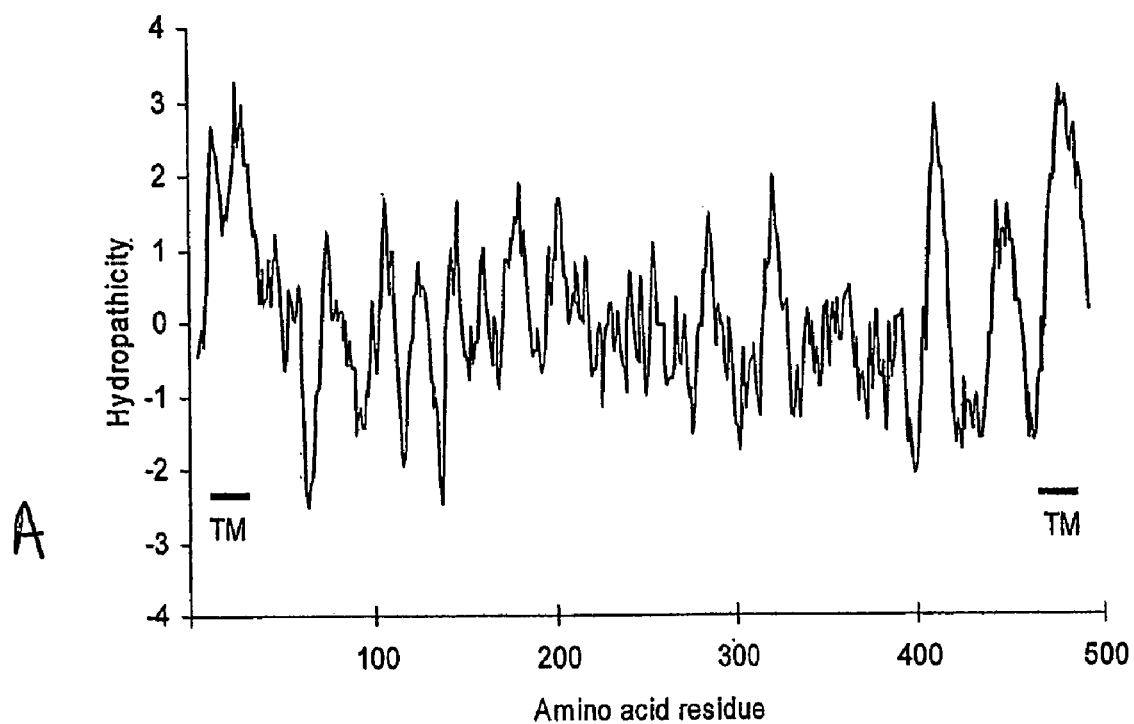
FIGS. 1A and 1B illustrate the hydrophobicity analysis and schematic representation of murine NTPDase8.
Figure 1:
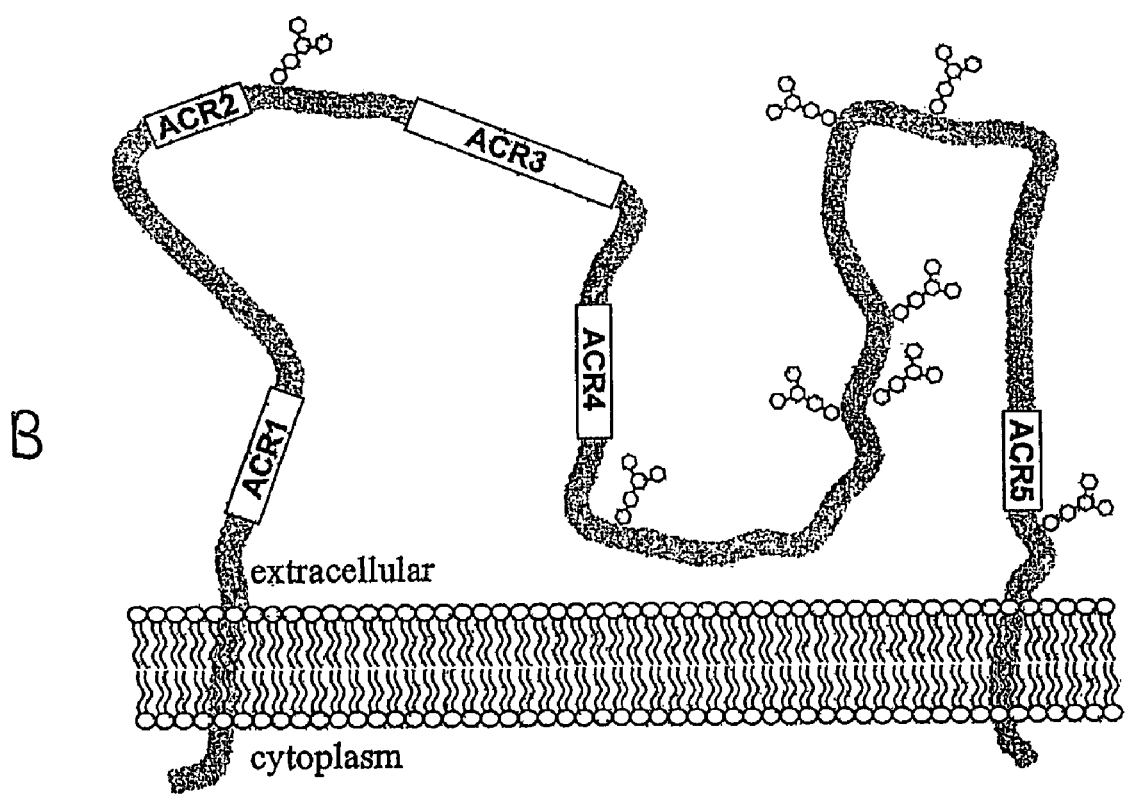

In accordance with the present invention, there is provided an isolated nucleoside triphosphate diphosphohydrolase (NTPDase) from a mammalian tissue characterized in that it comprises the amino acid sequence SEQ ID NO:1 and 3, with corresponding encoding nucleotide sequences SEQ ID NO:2 and 4.

The present invention relates to methods for reducing the platelet activation or aggregation state in an individual, and methods for treating or preventing a vascular condition by administering to said individual a NTPDase8 under the peptide form or under its nucleic acid form.

Hence, the present invention relates to methods of reducing or inhibiting platelet activation by administering to an individual an effective amount of a NTPDase8, or analoges or derivatives thereof.

The platelet activation state refers to the occurrence of one or more of the following events: platelet aggregation, platelet adhesion, platelet agglutination, platelet release reactions (e.g., osteonectin, platelet factor 4 or beta-thrombomodulin), expression of platelet external receptors (e.g., GPIIb/IIIa or P-selectin), or platelet interaction with other blood components (e.g., collagen or fibrinogen) and cells (e.g., leukocytes). Administration of a NTPDase8 decreases, reduces or inhibits one or more of these occurrences, thereby reducing the platelet activation state.

Several platelet activation markers exist which can be measured to assess the platelet activation state. Platelet activation can be assessed using platelet activation markers that are currently assessed in the art, as well as those that will later be discovered. Examples of platelet activation markers are: CD9, GPIb, GPIIb, CDIa-IIa, P-selectin, PECAM-1, GPIIb/IIIa, vitronectin, integrins and adhesive molecules. A reduction in the platelet activation state also refers to a decrease in or an absence of one or more platelet activation markers. One or more platelet activation markers is decreased by at least about 10% (e.g., 20% to 100%), as compared to the level just prior to administration. Hence, one can measure the presence, absence or level of one or more platelet activation markers, and compare the result against a control. For example, one can obtain a suitable sample and compare the level of one or more platelet activation markers from previous time points (e.g., prior to administration of the NTPDase8 or during the onset of a vascular event, disease or disorder). The level of one or more platelet activation markers decreases after administration of the NTPDase8, as compared to the level during the onset of the vascular event. One can also measure platelet activation markers in an individual prior to the onset of a vascular event (e.g., in a resting state or during a check-up), and determine the individuals baseline. Accordingly, administration of a NTPDase8 after the onset of a vascular disease decreases the levels of one or more platelet activation markers, as compared to those levels occurring during the onset of the vascular disease.

The level of platelet activation markers assessed can also be compared to a standard or control obtained from normal individuals. In one example, levels of platelet activation markers can be assessed in a population of healthy individuals or individuals who have not had a vascular event, disease or disorder. Such levels are referred to as a "negative control." Conversely, platelet activation marker levels can also be obtained from a pool of individuals who are undergoing a vascular event, disease or disorder, e.g., a "positive control." After administration of a NTPDase8, the level of one or more platelet activation markers decreases; the platelet activation marker level gets closer to the level of the negative control, and farther from the positive control. The level of a platelet activation marker decreases as compared to the level the platelet activation marker during the onset of the vascular event, disease or disorder. Hence, the methods include reducing the platelet activation state, or inhibiting platelet activation with administration of a NTPDase8, wherein one or more platelet activation markers is reduced or decreased, as compared to those levels during the occurrence of the vascular event, disease or disorder, or immediately prior to the administration of a NTPDase8.

In another embodiment, the present invention relates to a method for preventing the onset of a vascular event, disease or disorder. An effective amount of at least one NTPDase8 can be administered to prevent platelet activation state from increasing, or lessen platelet activation state that would otherwise become active without NTPDase8 administration. For example, an individual who is a risk for a vascular event, disease or condition can take a NTPDase8 on a daily basis (or every other day), to prevent the platelet activation state from increasing as compared to a control or baseline. Baseline levels of the platelet activation state can be obtained prior to and/or during the course of administration of a NTPDase8. The platelet activation state, as measured by platelet markers can stay the same, or can even decrease. Similarly, the platelet activation marker level can be compared to a negative or positive control, wherein upon administration of NTPDase8, the levels are closer to the negative control, than the positive control. However measured, the platelet activation state is prevented from increasing, thereby preventing the occurrence of a vascular event, disease or disorder.

The present invention also relates to reducing or inhibiting platelet activation by contacting the platelets with a NTPDase8 or derivatives or fragments thereof. This embodiment of the invention can be carried out in vivo or in vitro. The method reduces the level of one or more platelet activation markers, as compared to the level prior to contact of the NTPDase8 with the platelets.

The present invention pertains to methods for preventing or treating an individual at risk for a vascular event, disease or disorder. Platelet activation is the cause or a significant contributor of several vascular diseases. Prevention of a vascular event, disease or disorder (e.g., vascular condition) refers to delaying or suppressing the onset of the vascular condition, or one or more of its symptoms. To treat an individual at risk for a vascular condition means to alleviate or ameliorate one or more of its symptoms. An individual at risk for a vascular condition refers to an individual with a history of vascular disease, an individual experiencing symptoms or risk factors (e.g., gender, weight) associated with or caused by the vascular condition, an individual undergoing a vascular procedure, or an individual who has tested positive for a vascular condition using a diagnostic test (e.g., electrocardiogram, cardiac catheterization, stress test, ultrasound poppler techniques). A vascular condition is a event, disease or disorder that involves a thrombosis or a narrowing of a blood vessel. Vascular events, diseases or disorders include cardiovascular diseases (e.g., coronary heart disease, myocardial infarction, angina or a disease in which a narrowing of a blood vessel occurs in at least one major artery), cerebrovascular diseases (e.g., stroke or transient ischemic attacks), vascular procedures (e.g., thrombotic re-occlusion subsequent to a coronary intervention procedure, heart or vascular surgery) or any other thrombotic event (e.g., pulmonary embolism, deep vein thrombosis or peripheral vascular thrombosis). Vascular conditions also include Syndrome X, which is a disease that is associated with unidentified chest pain.

The NTPDases 8 used in the present invention can be administered with or without a carrier. The terms "pharmaceutically acceptable carrier" or a "carrier" refer to any generally acceptable excipient or drug delivery composition that is relatively inert and non-toxic. Exemplary carriers include sterile water, salt solutions (such as Ringer's solution), alcohols, gelatin, talc, viscous paraffin, fatty acid esters, hydroxymethylcellulose, polyvinyl pyrolidone, calcium carbonate, carbohydrates (such as lactose, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17.sup.th Ed., Mack Pub. Co., Easton, Pa.). Such preparations can be sterilized and, if desired, mixed with auxiliary agents, e.g., lubricants, preservatives, stabilizers, wetting agents, emulsifiers, salts for influencing osmotic pressure, buffers, coloring, preservatives and/or aromatic substances and the like which do not deleteriously react with the active compounds. Typical preservatives can include, potassium sorbate, sodium metabisulfite, methyl paraben, propyl paraben, thimerosal, etc. The compositions can also be combined where desired with other active substances, e.g., enzyme inhibitors, to reduce metabolic degradation. A carrier (e.g., a pharmaceutically acceptable carrier) is preferred, but not necessary to administer the compound.

The NTPDase8 can be a liquid solution, suspension, emulsion, tablet, pill, capsule, sustained release formulation, or powder. The method of administration can dictate how the composition will be formulated. For example, the composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

The NTPDase8 used in the invention can be administered intravenously, parenterally, intramuscular, subcutaneously, orally, nasally, topically, by inhalation, by implant, by injection, or by suppository. The composition can be administered in a single dose or in more than one dose over a period of time to confer the desired effect.

The actual effective amounts of compound or drug can vary according to the specific composition being utilized, the mode of administration and the age, weight and condition of the patient. For example, as used herein, an effective amount of the drug is an amount which reduces the platelet activation state. Dosages for a particular individual patient can be determined by one of ordinary skill in the art using conventional considerations, (e.g. by means of an appropriate, conventional pharmacological protocol).

For enteral or mucosal application (including via oral and nasal mucosa), particularly suitable are tablets, liquids, drops, suppositories or capsules. A syrup, elixir or the like can be used wherein a sweetened vehicle is employed. Liposomes, microspheres, and microcapsules are available and can be used.

Pulmonary administration can be accomplished, for example, using any of various delivery devices known in the art such as an inhaler.

For parenteral application, particularly suitable are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like. Ampoules are convenient unit dosages.

The administration of the NTPDase8 and the vascular treating compound can occur simultaneously or sequentially in time. The vascular treating compound can be administered before, after or at the same time as the NTPDase8. Thus, the term "co-administration" is used herein to mean that the NTPDase8 and the vascular treating compound will be administered at times to achieve a reduction of the platelet activation state. The methods of the present invention are not limited to the sequence in which the NTPDASE8 and vascular treating compound are administered, so long as the vascular treating compound is administered close enough in time to produce the desired effect of reducing the platelet activation state.

Finally, in addition to being small, potent and specific, the preferred cyclic peptide platelet aggregation inhibitor should not produce substantial untoward in vivo side effects such as an increased cutaneous bleeding time, reduction in platelet count, or decreased peripheral blood flow in a mammal treated with the inhibitor. Thus, for example, the time it takes for bleeding to stop, on an incision made in a mammal treated with a platelet aggregation inhibitor, dosed to inhibit about 90–100% of platelet aggregation, should not be more than about twice that of the mammal prior to treatment. Similarly, peripheral blood flow and other hemodynamic factors should not be adversely affected by treatment with doses sufficient to achieve 90–100% inhibition of platelet aggregation.

The present invention will be more readily understood by referring to the following examples which are given to illustrate the invention rather than to limit its scope.

EXAMPLE 1

Effect of Calcium and Magnesium on ATPase and ADPase Activity of Murine NTPDase8

Materials and Methods

Agarose, aprotinin, ethylenediaminetetraacetic acid (EDTA), ethylene glycol-bis(2-aminoethylether)-N-N-N'-N'-tetraacetic acid (EGTA), 2-(4-morpholino)-ethane sulfonic acid (MES), nucleotides, phenylmethanesulfonyl fluoride (PMSF), sodium acetate, tetrabutylammonium hydrogen sulphate (TBA) and tris(Hydroxymethyl) aminomethane (Tris) were purchased from Sigma-Aldrich (Oakville, On, Canada). Glycine was provided by Fisher Scientific Ltd (Nepean, On, Canada). All cell culture media were obtained from Invitrogen (Burlington, On, Canada) and the 24-well plates from VWR Canlab (Mont-Royal, Qc, Canada).

RT-PCR Cloning

Total RNA was isolated from mouse liver with TriZol™ reagent (Invitrogen). cDNA was synthesized with SuperScript II (Invitrogen) from 500 ng of total RNA with oligo $(dT)_{18}$ as the primer, according to the manufacturer's instructions (Invitrogen). For amplification, one fifth of the reverse transcription (RT) reaction volume was used as template in a final volume of 50 µl containing 0.4 µ/M primer, 200 µM dNTP and 0.7 U Tgo DNA polymerase™ (Roche, Laval, Qc, Canada). The two following sets of primers were designed based on the 5' and 3' ends of incomplete mouse EST sequences (GenBank accession numbers BB610017 and AV026718, respectively): 1) forward 5'GGA-GAC-GGG-GTG-TGG-AGG-AC3' (SEQ ID NO:5), reverse 5'GGG-GTT-CAT-AAG-GGC-AGG-CA3' (SEQ ID NO:6); 2) forward 5'GTA-GGT-GGA-GAC-GGG-GTG-TG3'(SEQ ID NO:7), reverse 5'GGG-TTC-ATA-AGG-GCA-GGC-AT3'(SEQ ID NO:8). Amplification was started with 2 min at 94° C. followed by 35 cycles of 1 min denaturation at 94° C., 2 min annealing at 60° C., 2 min primer extension at 72° C. and ended with a 7 min incubation at 72° C. The PCR product of approximately 1.8 kb was purified on agarose gel using the QIAEX II™ gel extraction kit (Qiagen, Mississauga, On, Canada) and ligated to pcDNA3.1/V5-His (Invitrogen). Plasmid DNA was purified with the QIAprep Spin Miniprep kit™ (Qiagen) and the orientation of the insert determined by restriction enzyme mapping. Two independent clones (one for each set of primers) with the orientation allowing the expression of the protein were amplified and sequenced. One clone was completely sequenced in both directions and the second clone in one orientation to confirm the sequence obtained from the first clone. Both sequences were identical.

COS-7 Cell Transfection and Protein Preparation

COS-7 cells were transfected in 10 cm plates using Lipofectamine™ (Invitrogen), as previously described (Kaczmarek et al, 1996, JBC, 271:33116–33122). Briefly, cells were incubated for 5 h at 37° C. in DMEM in absence of foetal bovine serum (FBS) with 6 µg of plasmid DNA and 24 µl of Lipofectamine™ reagent. The reaction was stopped by adding an equal volume of DMEM containing 20% FBS and cell were harvested 40–44 h later. For protein preparation, transfected cells were washed three times with Tris-saline buffer at 4° C., harvested by scraping in 95 mM NaCl, 0.1 mM PMSF and 45 mM Tris, pH 7.5, and washed twice by 300×g centrifugation for 10 min at 4° C. Cells were resuspended in the harvesting buffer containing 10 µg/ml aprotinin and sonicated. Nucleus and cellular debris were discarded by another centrifugation as described above and the supernatants stored at −80° C. until used. Protein concentration was estimated by the Bradford microplate assay using bovine serum albumin (BSA) as a standard of reference (Bradford, 1976, Analyt. Biochem., 72:248–254).

NTPDase Activity Measurement

Enzyme activity in the protein fractions was determined as previously described (Sévigny et al, 1997, Biochimica Biophysica Acta 1334:73–88) Briefly, enzyme activity was measured at 37° C. in 0.5 ml of the following incubation medium: mM $CaCl_2$ either with 100 mM Tris, pH 7.4 or with 100 mM MES, pH 6.4 or as indicated. Enzyme preparation was added to the incubation mixture and pre-incubated at 37° C. for 3 min. Reaction was started by the addition of 0.5 mM substrate (ATP, ADP, UTP, UDP or AMP) and stopped after 20 min by the addition of 0.125 ml of the malachite green reagent (Baykov and Evtushenko, 1988, Analytical Biochemistry 171:266–270). Activity on intact cells was carried out in similar conditions in 24 wells plates, also 40–44 h after transfection, with the addition of 145 mM NaCl to the incubation medium. The reaction was stopped by taking 0.2 ml of the reaction mixture to a new tube containing 50 μl of malachite reagent. The inorganic phosphate (Ps) released from the hydrolysis of exogenous nucleotides was measured according to Baykov et al. (Baykov and Evtushenko, 1988, Analytical Biochemistry 171:266–270)

Optimum pH was determined in the presence of 5 mM $CaCl_2$ with the following buffers: 100 mM acetate (pH 4.0–5.5), 100 mM MES (pH 5.5–7.0), 100 mM Tris (pH 7.0–9.0) or 100 mM glycine pH (9.0–11.0). In the indicated experiments $CaCl_2$ was substituted by $MgCl_2$. To remove traces of divalent cations 1 mM EDTA plus 1 mM EGTA was added to the medium. One unit of enzyme activity corresponds to the release of 1 μmole $P_i$/min at 37° C. (LeBel et al., 1980, J. Biol. Chem. 255:1227–1233). All experiments were performed in triplicate with the appropriate controls.

Separation and Quantification of Nucleotides by HPLC

For HPLC analysis, activity assays were performed in 5 mM $CaCl_2$ and 100 mM MES, pH 6.4 as described above with the following modifications. Aliquots of 20 μL were taken at different time points from the enzymatic reaction and activity stopped by the addition of an equal volume of ice-cold 1 M perchloric acid. The samples were centrifuged for 5 min at 1000×g at 4° C. Supernatants were neutralized with 1 M KOH (4° C.), centrifuged for a subsequent 5 min at 1000×g and then lipids were removed by liquid-liquid extraction with n-heptane (5:1, v/v). An aliquot of 20 μL from the lipid extracted sample was applied to a column connected to a HPLC system.

Adenine nucleotides (ATP, ADP and AMP) were separated on a 15 cm×4.6 mm, 3 μm SUPELCOSIL™ LC-18-T column (Supelco, Bellefonte, Pa., USA) with a mobile phase composed of 25 mM TBA, 5 mM EDTA, 100 mM $KH_2PO_4$/$K_2HPO_4$, pH 7.0 and 2% methanol (v/v), at a flow-rate of 1 ml/min. Uridine nucleotides (UTP, UDP and UMP) were resolved using SUPELCOSIL™ LC-18-T column (25 cm×4.6 mm, 5 μm, Supelco) as described above with the difference that the mobile phase did not contain methanol. Combined adenine and uridine nucleotide samples were analyzed with the latter column with a mobile phase composed of 16.7 mM TBA, 3.3 mM EDTA, 66.7 mM $KH_2PO_4$/$K_2HPO_4$, pH 7.0. The flow rate was 0.5 ml/min for the first 20 min and 1 ml/min up to 90 min. The nucleotides were detected by UV absorption at 260 nm and identified by comparison of the retention time and UV spectrum with the appropriate standards.

Results

Cloning and Characterization of Mouse Entpd8 cDNA

Figure 2:
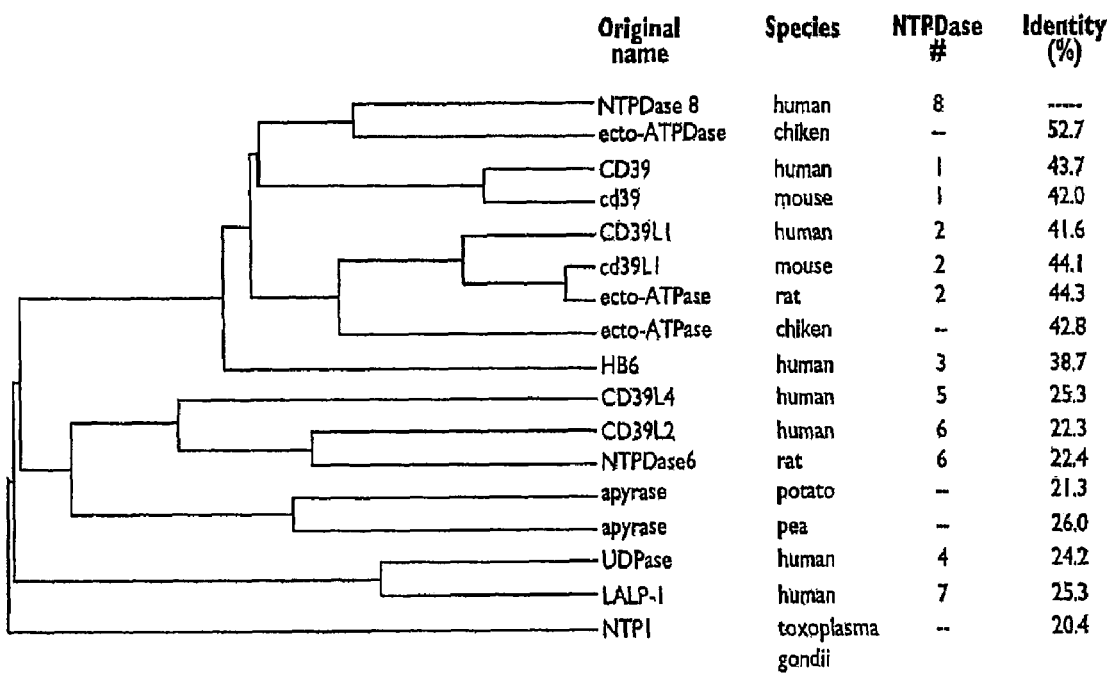
FIG. 2 illustrates the phylogenetic analysis of amino acid sequences of selected NTPDases and related proteins.

The sequence includes a protein of 497 amino acid residue (SEQ ID NO:1) with a predicted molecular mass of 54 650 Da and a calculated isoelectric point of 5.94, and a respectively encoding nucleotide sequence (SEQ ID NO:2) having an open reading frame of 1491 nucleotides which is translated into. The deduced amino acid sequence contains eight potential N-glycosylation sites, the five apyrase conserved regions and various potential phosphorylation sites including one for both Protein kinase C and Casein kinase II on serine 4. Hydrophobicity analysis of mouse NTPDase8 predicts two transmembrane domains in the polypeptide chain, one near the N terminus (amino acids 9–30) and one near the C terminus (amino acids 469–490; FIG. 1A). A schematic representation of the protein is shown on FIG. 1B. Distance estimation of the amino acid sequences of various NTPDases and related proteins was performed with GeneBee software (http://www.genebee.msu.su/). The phylogenetic tree obtained is shown in FIG. 2. The percentage of amino-acid identity of these proteins with mouse NTPDase8 was determined by pair wise alignment using ALIGNp (http://www.infobiogen.fr/services/analyseq/cgi-bin/alignp_in.pl). The mouse NTPDase8, chicken ecto-ATPDase, human CD39L1, mouse CD39L1, rat ecto-ATPase, chicken ecto-ATPase, human CD39, mouse CD39, human HB6, human CD39L4, human CD39L2, rat NTPDase6, potato apyrase, pea apyrase, human UDPase, human LALP1, and *toxoplasma gondii* apyrase, were compared. Murine NTPDase8 had highest homology with chicken ecto-ATPDase with 52.7% amino acid identity.

Genomic Characterization of Entpd 8

Figure 3:
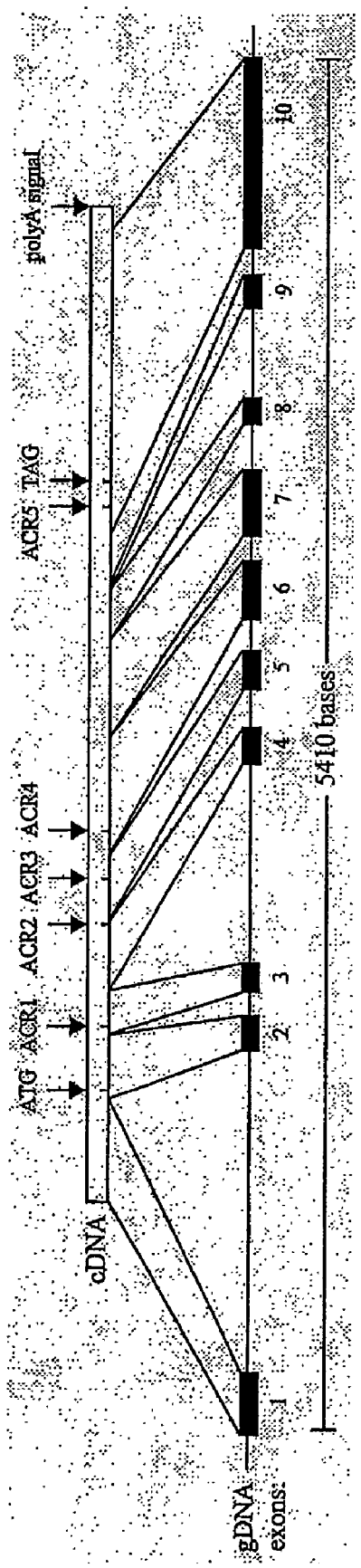
FIG. 3 illustrates a schematic representation of the genomic organization of mouseencoding gene Entpd8.

The full cDNA against the mouse genomic sequence reveals that mouse Entpd8 covers approximately 5410 bases and is organized into 10 exons and 9 introns, all in agreement with the GT/AG rule. The coding sequence, including exon 2 to 10, Was cloned from mouse genomic DNA, and its sequence confirmed the intron/exon junctions found in the entry. FIG. 3 and Table 1 summarize the genomic structure of mouse NTPDase8 gene.

TABLE 1

Summary of the genomic structure of mouse Entpd8.

| Exon | Splice acceptor | Length of exon (bases) | Exon position in NT_039205.1 | Splice donor | Length of intron (bases) | Nucleotide position of important sequences in current exon |
|---|---|---|---|---|---|---|
| 1 | ccaggtcag/TTCCAAAGT | 246 | 2557096–2557341 | CCAGTGCAG/gtgagcgac | 1254 | Promoter -260 to -179 |
| 2 | cccttgcag/CTCAGACCC | 142 (from Met 126) | 2558596–2558737 | GACACCAAG/gtttgctca | 85 | Met 17–19 |
| 3 | tatccctag/TTTGGGATT | 118 | 2558823–2558940 | AGATAGAAG/gtcagtgga | 777 | ACR1 16–39 |
| 4 | gtgtttcag/GACCTGGAA | 151 | 2559718–2559868 | GCTGCTCAG/gtgacacag | 141 | ACR2 126–143 |
| 5 | tctgcccag/CCAGAAGAA | 160 | 2560010–2560169 | CTCCTGAAG/gtgcagggg | 118 | ACR3 98–112 |

TABLE 1-continued

Summary of the genomic structure of mouse Entpd8.

| Exon | Splice acceptor | Length of exon (bases) | Exon position in NT_039205.1 | Splice donor | Length of intron (bases) | Nucleotide position of important sequences in current exon |
|---|---|---|---|---|---|---|
| 6 | tgtggtcag/TATTCCTCT | 237 | 2560288–2560524 | GACAGGTTG/gtatgtgaa | 90 | ACR4 55–78 |
| 7 | tctctgcag/AGCAGCCAG | 264 | 2560615–2560878 | CAGTTCTAT/gtaagcatg | 172 | |
| 8 | cttccccag/GCATTTTCC | 111 | 2561051–2561161 | TGGAAACTG/gtgggtgac | 354 | |
| 9 | gaacccaag/GTGGAAGTC | 135 | 2561516–2561650 | CAGAAGCAG/gtgactgcc | 100 | ACR5 22–33 |
| 10 | gtctcacag/GCAGGTGAC | 755 (up to TAG 189) | 2561751–2562488 | TAG | Introns + exons 5410 | TAG 190–192 polyA 540 bp after TAG |

Sizes and junctions of the exons and introns of mouse Entpd8(= NTPDase8) are presented according to the sequence of accession No. NT_039205.1. Intron sequences are given in small characters and exons in capitals.

Biochemical Characterization of NTPDase8

Figure 4:
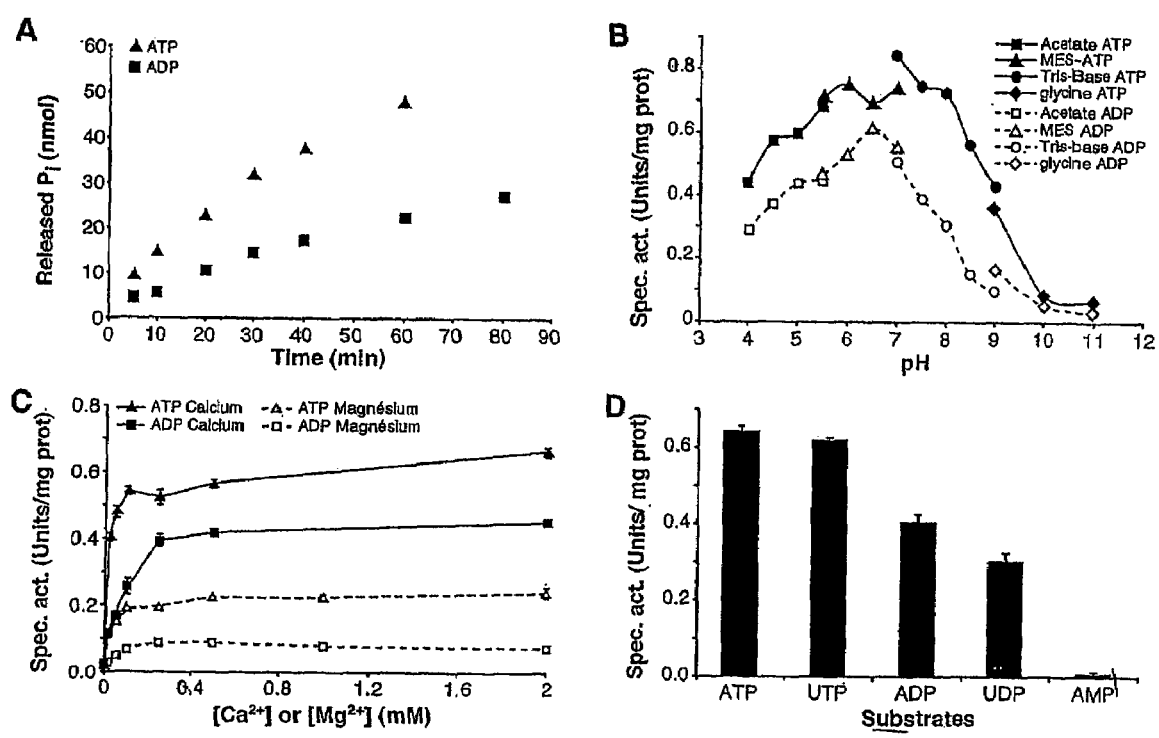
FIGS. 4A to 4D illustrate the biochemical characterization of mouse NTPDase8.

The biochemical characteristics of this novel NTPDase were determined with crude protein extracts, in COS-7 cells transiently transfected with an expression vector (pcDNA3.1/V5-His) containing the Entpd8 cDNA. Firstly, we determined the time course of the reaction by stopping the reaction at different time points from 5 to 60 min. The result on FIG. 4A shows that the reaction was linear for the first 30 min with both ATP and ADP as substrates. All of the following assays were, therefore, carried out for 12 to 20 min. The effect of pH on ATPase and ADPase activity was, then, evaluated from pH 4.0 to 11.0. FIG. 4B shows that murine NTPDase8 is highly active between pH 5.5–7.0 with optimal activity around pH 6.4 for ADPase activity. The enzyme showed a marked preference for $Ca^{2+}$ over $Mg^{2+}$ for the nucleotides tested (FIG. 4C). In the presence of 1 mM EDTA and 1 mM EGTA, that remove traces of divalent cations, no activity could be detected with any of the substrates tested (FIG. 4C). The substrate specificity of NTPDase8 in the presence of $Ca^{2+}$ is illustrated on FIG. 4D. Although all triphospho- and diphosphonucleosides tested were hydrolyzed, NTPDase8 preferred triphosphonucleosides with a ratio in the order of ~2:1 (ATP/ADP=1.6±0.3 and UTP/UDP=2.1±0.3). Like other NTPDases, this enzyme did not hydrolyze AMP (FIG. 4D). As a control, the biochemical activity measured in untransfected COS-7 cell extracts was less then 7% of the activity detected in transfected cells with a maximum of 0.05 U/mg of protein at pH 8.0 with ATP as substrate.

Figure 5:
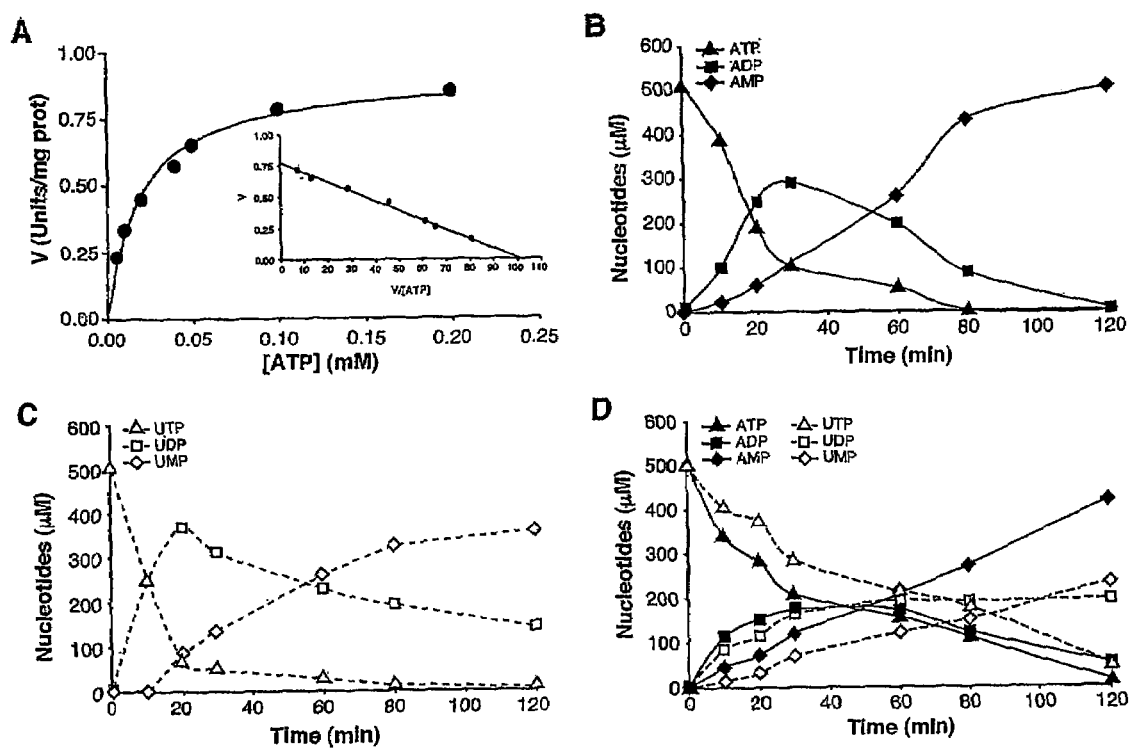
FIGS. 5A to 5D illustrate the kinetics and profile of nucleotides hydrolysis by mouse NTPDase8.

All four nucleotides tested were hydrolyzed by NTPDase8 consistently with Michaelis-Menten model of kinetics (FIG. 5A, not shown for ADP, UTP and UDP). The apparent $K_m$ constants were calculated by plotting the data according to Woolf-Augustinsson-Hofstee method (FIG. 5A) and are summarized in Table 2. Triphosphonucleosides had lower apparent $K_m$ compared to their respective diphosphonucleoside by over three folds while the apparent $V_{max}$ were comparable for the four substrates tested. Based on these observations it could be predicted that ATP and UTP hydrolysis by NTPDase8 would result in an accumulation of the corresponding diphospho-derivative. As these intermediate products can also activate subset of P2 receptors, we followed their apparition by HPLC analysis over a time period of two hours. Incubation of ATP or UTP with protein extracts from NTPDase8 expressing COS-7 or with intact transfected cells, led to the formation of high levels of the corresponding diphosphonucleoside during the early phase of the reaction (FIG. 5B, C). In these experiments, ADP and UDP were further hydrolyzed to the corresponding monophosphonucleoside, only when ATP and/or UTP concentration had significantly decreased. After 120 min, ADP was completely hydrolyzed to AMP (FIG. 5B) while UDP was still detectable at a concentration of 140 μM (FIG. 5C). When both ATP and UTP were added together, adenine nucleotides were slightly preferentially hydrolyzed giving rise to an accumulation of UDP for an important period of time (FIG. 5D). These data were also in agreement with the lower $K_m$ values for adenine nucleotides compared to uridine nucleotides.

TABLE 2

Kinetic constants of NTPDase8.

| Substrate | $K_{m,app}$ (μM) | $V_{max,app}$ (U/mg of protein) |
|---|---|---|
| ATP | 13 ± 6 | 0.82 ± 0.02 |
| ADP | 41 ± 6 | 0.95 ± 0.08 |
| UTP | 47 ± 1 | 1.13 ± 0.02 |
| UDP | 171 ± 15 | 1.08 ± 0.06 |

$K_{m,app}$ and $V_{max,app}$ were estimated using Woolf-Augustinsson-Hofstee plot.
Results are express as the mean ± SEM.
The curves drawn from these data gave a $r^2$ of 0.99, 0.98, 0.99 and 0.96 for ATP, ADP, UTP and UDP respectively.

It is noteworthy that comparable experiments were conducted as in FIG. 4D and FIGS. 5B–D with confluent intact COS-7 cells transiently transfected with NTPDase8. Similar substrate specificity and pattern of hydrolysis were observed as detected by either $P_i$ determination or HPLC analysis of the products. In addition, the tight association of NTPDase8 to a membrane fraction was confirmed by an ultracentrifugation of the protein extracts at 100 000×g for 1 hour. Indeed, over 90% of the total activity collected was found in the pellet fraction. These experiments demonstrated that mouse NTPDase8 is an ectoenzyme tightly bound to the plasma membrane.

EXAMPLE II

Effect of Murine NTPDase8 on Platelet Aggregation

Transient Transfection

COS-7 cells were grown in Dulbecco's modified Eagle's medium supplemented with 10% fetal calf serum (FCS). Cells were seeded at $5 \times 10^5$ cells per 30-mm well and transfected 20–24 h later with Lipofectamine™ (Life Technologies, Inc.) according to the manufacturer's instructions. Briefly, the cells were exposed to 1 µg of DNA (pcDNA3 or pcDNA3-CD39) and 4 µl of Lipofectamine in Dulbecco's modified Eagle's medium without FCS for 5 h, followed by the addition of an equal volume of Dulbecco's modified Eagle's medium containing 20% FCS. Twenty-four h after transfection, the culture medium was changed (Dulbecco's modified Eagle's medium/10% FCS), and ~70 h post-transfection, COS-7 cells were used for analyses. Control COS-7 cells used for transfection were negative for CD39 as analyzed by Western blotting and FACS with anti-CD39 mAb; ATPDase biochemical activity was negligible.

Cell membrane preparation and platelet aggregation assays were performed as described before.

Results

Figure 6:
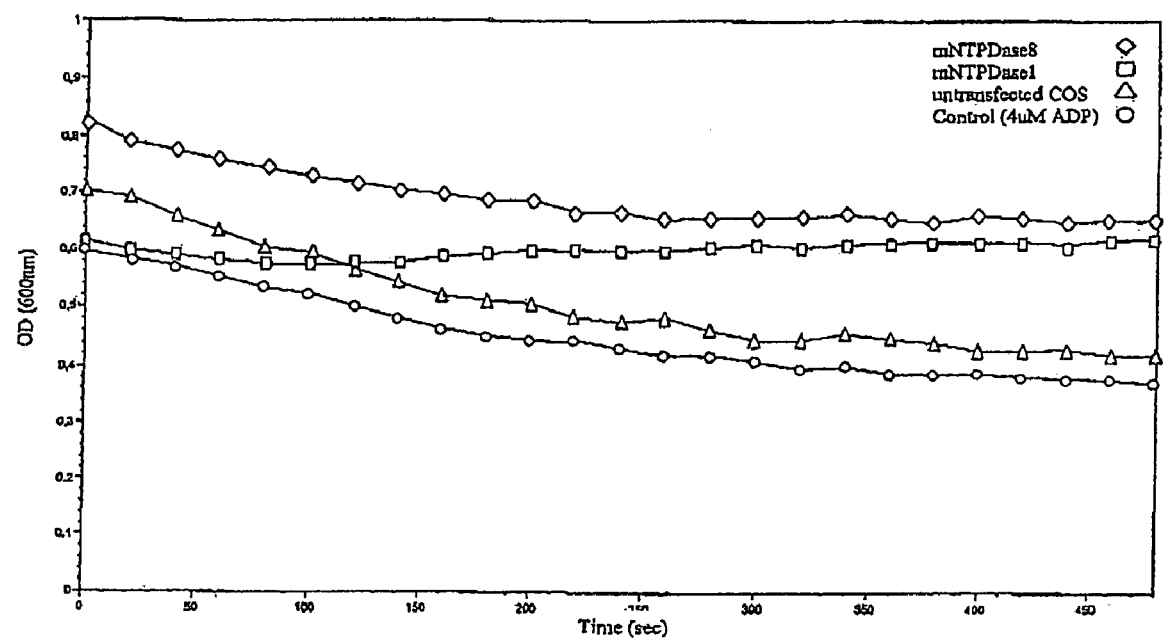
FIG. 6 illustrates the effect of the isolated NTPDase8 on platelet aggregation.

PRP prepared from human donors was tested for platelet activation in the presence of exogenous ADP and protein extracts from COS cell transfected with pcDNA3.11V5-His encoding mouse NTPDase8 (mNTPDase8) or mouse (mNTPDase1) (FIG. 6). Optic density at 600 nm was recorded over a period of 8 minutes. Before the addition of 4 uM ADP, PRP was preincubated for 25 seconds with 250 ug mNTPDase8 or 3 ug mNTPDase1 protein extracts, 250 ug untransfected COS cells or without protein extract (agonist: 4 uM ADP). Note that 4 uM ADP induced high levels of platelet aggregation in control samples. This could be reversed by the addition of mNTPDase8 (53% inhibition) and mNTPDase1 (100% inhibition).

EXAMPLE III

Human NTPDase8

Human NTPDase8 was isolated and analyzed as described in the previous EXAMPLES. It shows having amino acid sequence SEQ ID NO:3 and nucleotide sequence SEQ ID NO:4. Its activity has been found to be similar to the activity of the mouse equivalent described herein.

The activity of the protein extracts of human NTPDase8 was carried out as described previously herein and the results are shown in Table 3.

TABLE 3

| Activity on protein extracts from human NTPDase8 transient transfected COS-7 cells. | |
|---|---|
| Substrate (number of independent experiments each in triplicate) | Activity (nmols $P_i$/min/mg) |
| ATP (4) | 264 ± 7 |
| ADP (4) | 55 ± 15 |
| AMP (3) | 2 ± 0.6 |
| UTP (3) | 271 ± 35 |
| UDP (3) | 38 ± 5 |

Molecular mass: 53.9 kDa;
Isoelectric point: 5.42;
Homology with mouse NTPDase8: 81.3% amino acid identity (63.4% at the nucleotide level, coding sequence only)

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. An isolated peptide comprising the amino acid sequence SEQ ID NO:1 or SEQ ID NO:3, a functional fragment or an analog thereof, said isolated peptide having an ectonucleotidase activity, for use in modulation of a biological reaction being selected from the group consisting of platelet aggregation, platelet related thrombosis, emboli, and angiogenesis.

2. A method for modulating at least one biological reaction selected from the group consisting of platelet aggregation, thrombosis, emboli, and angiogenesis, said method comprising depositing in blood or a medium comprising blood in a sufficient amount of a peptide encoded by a nucleic acid molecule as defined in claim 1 or an isolated peptide as defined in claim 1 in condition allowing the modulation of platelet aggregation, thrombosis, or emboli.

* * * * *